US009901736B2

United States Patent
Chen et al.

(10) Patent No.: US 9,901,736 B2
(45) Date of Patent: Feb. 27, 2018

(54) COCHLEA HEARING AID FIXED ON EARDRUM

(71) Applicants: Kuang-Chao Chen, New Taipei (TW); Silicon Motion, Inc., Hsinchu County (TW)

(72) Inventors: Kuang-Chao Chen, New Taipei (TW); Kuo-Liang Yeh, Hsinchu County (TW)

(73) Assignees: Kuang-Chao Chen, New Taipei (TW); SILICON MOTION, INC., Hsinchu County (TW)

( * ) Notice: Subject to any disclaimer, the term of this patent is extended or adjusted under 35 U.S.C. 154(b) by 2 days.

(21) Appl. No.: 15/154,505

(22) Filed: May 13, 2016

(65) Prior Publication Data

US 2016/0331965 A1    Nov. 17, 2016

(30) Foreign Application Priority Data

May 14, 2015   (TW) .............................. 104115415 A (51) Int. Cl.
| *A61N 1/36* | (2006.01) |
| *A61N 1/372* | (2006.01) |
| *A61N 1/05* | (2006.01) |
| *G06F 17/28* | (2006.01) |
| *G02C 11/06* | (2006.01) |

(52) U.S. Cl.
CPC ....... *A61N 1/36032* (2013.01); *A61N 1/0541* (2013.01); *G06F 17/289* (2013.01); *A61N 1/37217* (2013.01); *G02C 11/06* (2013.01)

(58) Field of Classification Search
None
See application file for complete search history.

(56) References Cited

U.S. PATENT DOCUMENTS

| 5,259,032 | A | * | 11/1993 | Perkins | ................ | H04R 25/606 |
| | | | | | | 381/312 |
| 6,157,727 | A | * | 12/2000 | Rueda | ................... | H04R 25/55 |
| | | | | | | 381/23.1 |
| 6,697,674 | B2 | * | 2/2004 | Leysieffer | .......... | A61N 1/36032 |
| | | | | | | 600/25 |
| 7,149,320 | B2 | * | 12/2006 | Haykin | ................ | H04R 25/552 |
| | | | | | | 381/314 |
| 7,376,563 | B2 | * | 5/2008 | Leysieffer | .......... | A61N 1/36032 |
| | | | | | | 381/312 |
| 7,983,435 | B2 | * | 7/2011 | Moses | .................. | H04R 25/606 |
| | | | | | | 381/326 |
| 8,295,523 | B2 | * | 10/2012 | Fay | ...................... | H04R 25/604 |
| | | | | | | 381/324 |
| 8,781,836 | B2 | * | 7/2014 | Foo | ...................... | H04R 25/505 |
| | | | | | | 704/258 |

(Continued)

FOREIGN PATENT DOCUMENTS

CN          102598713 A       7/2012

*Primary Examiner* — Brian T Gedeon
(74) *Attorney, Agent, or Firm* — Chun-Ming Shih (57) ABSTRACT

A cochlea hearing aid device for helping users to hear includes a cochlea electrode and a driver circuit. The driver circuit has a casing for installing at a through hole on an eardrum of the user. The cochlea electrode is installed within the cochlea of a user. The driver circuit is connected to the cochlea electrode in order to signal process a voice data and provides a corresponding driving signal for cochlea electrode. Therefore, the neural cells in the cochlea of the user will be stimulated and helped the user to hear.

19 Claims, 8 Drawing Sheets

(56) References Cited

U.S. PATENT DOCUMENTS

| | | | | |
|---|---|---|---|---|
| 8,787,609 | B2* | 7/2014 | Perkins | H04R 25/606 381/326 |
| 9,191,755 | B2* | 11/2015 | Kalluri | H04R 25/552 |
| 9,247,353 | B2* | 1/2016 | Bewley | H04R 25/556 |
| 9,550,051 | B2* | 1/2017 | Jolly | A61M 5/14276 |
| 2003/0195588 | A1* | 10/2003 | Fischell | A61N 2/02 607/55 |
| 2005/0033384 | A1* | 2/2005 | Sacha | A61N 1/36032 607/57 |
| 2005/0091060 | A1* | 4/2005 | Wing | H04R 25/505 704/271 |
| 2009/0024183 | A1* | 1/2009 | Fitchmun | A61N 1/36032 607/56 |
| 2010/0324355 | A1* | 12/2010 | Spitaels | H04R 25/606 600/25 |
| 2014/0236594 | A1* | 8/2014 | Clarke | G02B 27/017 704/233 |
| 2014/0288358 | A1 | 9/2014 | Puria | |
| 2015/0181353 | A1* | 6/2015 | Choi | G06Q 30/0207 381/312 |

* cited by examiner

COCHLEA HEARING AID FIXED ON EARDRUM

CROSS-REFERENCE TO RELATED APPLICATIONS

This non-provisional application claims priority claim under 35 U.S.C. §119(a) on Taiwan Patent Application No. 104115415 filed on May 14, 2015, the entire contents of which are hereby incorporated by reference.

BACKGROUND

Technical Field

This disclosure relates to cochlea hearing aid device; in particular, to a cochlea hearing aid device that installs at the eardrum of the user.

Related Art

A lot of people, when born, lose hearing because of genetic defects or because of traumas or diseases. For those children suffer from hearing loss, it is critical to speech and language development. Therefore, how to provide hearing reconstruction for people who cannot hear is a very valuable job.

SUMMARY

According to the first embodiment of the present invention, this disclosure provides a cochlea hearing aid device for helping user to hear. The cochlea hearing aid device has a cochlea electrode and a driver circuit. The driver circuit has a casing for installing at a through hole on an eardrum of the user. The driver circuit is connected to the cochlea electrode in order to signal processing a voice data and provide a corresponding driving signal for cochlea electrode. The driving signal drives the cochlea electrode to generate an electrical stimulation corresponding to the voice data at the cochlea for helping user to hear the corresponding "sound" of the voice data.

The cochlea electrode could be made of different electrode metal wire, for the contacting part that touches cochlea could be made of a relative steady material such as silicone. The cochlea electrode could provide suitable electrical stimulation for stimulates the auditory nerve cells.

The driver circuit has a casing for installing at a through hole on an eardrum of the user. Corresponding circuit and batteries could be hanged at the above said casing or the extending part of the above said casing. The casing could locate the driver circuit at an appropriate position, and the driver circuit is unlikely to be moved while cleaning the foreign bodies in the inner ear.

The above said driver circuit could have different designs, such as driver circuit could be made of a verity of digital signal processing circuits, or only include simple current/voltage signal processing units, such as Digital-to-Analog Converter (DAC).

Besides the driver circuit and the cochlea electrode 105, the cochlea hearing aid device further comprises a digital processing circuit for adjusting the voice data. For instance, the digital processing circuit could process a noise reduction, waveform adjustment, or echo cancellation etc. Furthermore, the digital processing circuit could integrated into a corresponding integrated circuit chip.

The cochlea hearing aid device also comprises a voice amplifier and a voice collector. The voice collector might be a microphone for collecting the external sound. The external sound is amplified by the voice amplifier then provides the voice data.

In order to achieve clear external sound, the voice collector such as microphone could be mounted at external of the ear and transfers the corresponding information via wire or wireless manner to the driver circuit. Then, the cochlea electrode stimulates an appropriate electrical stimulation.

If the information is transmitted via wireless manner, the wireless manner could be any well-known communication protocol, such as blue tooth, wireless USB, ZigBee, Wi-Fi, or any special designed or personal communication protocol.

Other possible solution of the present invention is to include a wireless circuit for eardrum in cochlea hearing aid device. The wireless circuit receives and converts the wireless signal to the voice data. Wherein, the wireless signal is provided by mobile phone or other hand-held electronic apparatus.

Or the cochlea hearing aid device could include a processing circuit that disposed on a pair of glass or a pair of smart glass. The processing circuit could provide the voice data to the driver circuit Cochlea electrode could operate in different working modes, wherein different working mode could design different parameters and different working algorithm for processing voice. For instance, while the cochlea electrode connects to an external device such as mobile phone, some of the computing progress could be outsource to mobile phone. In order to save power, the cochlea electrode that corresponding to the inner ear portion only need to provide basic function like voice output. Further, the voice data could also process difficult data processing via an external hand-held electronic apparatus to meet the requirement of different design of the hearing aids.

The wireless signal further comprises a controlling signal for adjusting the output parameter of the cochlea electrode. For instance, the cochlea hearing aid devices at different ears could be adjusted to provide corresponding output parameter to avoid the uncomfortable feeling cause by hearing difference in each ear.

The cochlea hearing aid device further include a power circuit for eardrum that provides the power to the cochlea electrode and the driver circuit via wire or wireless manner. As the technique of the wireless charging improved, many wireless charging methods can apply with the cochlea hearing aid device and provide a more life convenient hearing aid.

For those with normal hearing, acoustic perception includes direction and distance. In order to imitate normal acoustic perception, voice processing of the cochlea hearing aid device further includes a voice signals with a direction perception. For example, in one of the embodiments, multiple microphones could be placed in different positions for collecting external sound. Since placing in different positions, there are transmitting shifts among the collected sounds. When user use a pair of cochlea hearing aid device, the cochlea hearing aid device could adjust each of the corresponding parameter of the cochlea electrode (respect to different ears). Through the adjustment, voice signals with different direction perceptions could be provide to each eardrum for hearing. Therefore, one could percept the direction and distance of the object that provides sounds in order to response or act. The object that provides sounds could be vehicles or stepping sounds.

Furthermore, one's acoustic perception could also affect one's balance control. For a more comfortable cochlea hearing aid device wearing experience, the cochlea hearing aid device could provide different parameters and adjustment according to different ears. These parameter adjustments might need to adjust according to different scenarios and a might need a relative longer adjusting period. The corresponding configuration could be saved at a mobile phone or hand-held electronic apparatus. User could set several scenario parameters and adjust different output parameters for different ears according to need. For example, watching television, attending class, during conversation, self-talking while learning language could be set as different scenarios. With the above means, user could simply select between the scenarios for the corresponding parameter to output suitable voice output. An auto select could be apply through the help of information like GPS, Wi-Fi signal and time.

In addition, the voice signals are processed signals, therefore the voice signals do not have to be exactly like the origin voice signal from the outside. In other way of speaking, the voice data could go through a translating process in order to translate the origin voice signal from the outside to a corresponding a voice signal with a replaced content.

For example, the voice data could extract portion of the origin voice signal from the outside and repeatedly play. Or in other example, the voice data will extract at least one keyword from the origin voice signal from the outside, and at least one keyword is accentuated and played. The original voice signal is analyze and keywords are extracted, and only keywords are outputted. For those elders that suffer from cognitive impairment, repeating keywords from the origin voice signal several times could help them to pick up the message inside the voice signal more easily. Others, the voice signal could be recorded, selected and replayed by the user. The origin voice signal from the outside could be sounds directly provided by the object or could be sounds generates by the electric device such as alarm sound. Other than that, the voice signal could be the result of language translating process, a result of dialect translating process, a result of accentuated process or a result of speed adjusted process.

For instance, some elders can only speak and understand dialects, but their grandchildren could only speak official language. In this case, the translating process could be set to a mode that could translate the dialect to the official language (i.e., a dialect translating process). Further, with the aid of recording and replaying, the communication between the elder and the youth will be improved and provide positive effect on the quality of life.

BRIEF DESCRIPTION OF THE DRAWINGS

This disclosure will become more fully understood from the detailed description given herein below for illustration only, and thus not limitative of this disclosure, wherein.

DETAILED DESCRIPTION

Figure 1:
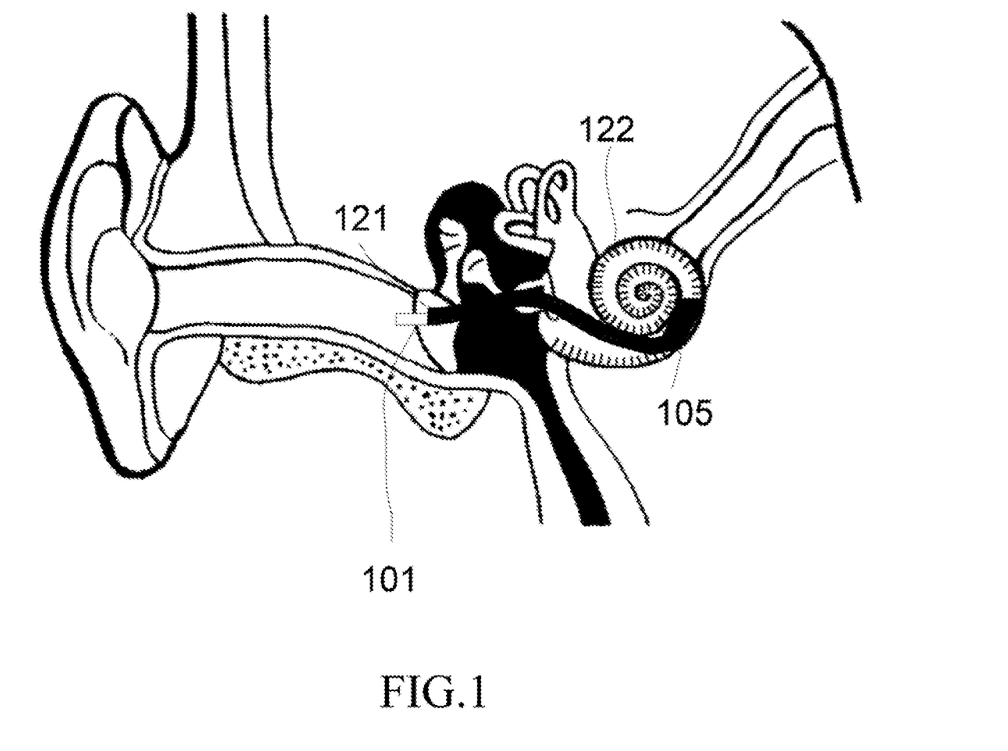
FIG. 1 is a perspective view of the cochlea hearing aid device in accordance with a first embodiment.

Referring to FIG. 1, FIG. 1 is a perspective view of cochlea hearing aid device in accordance with a first embodiment, for helping people to hear. The cochlea hearing aid device includes a cochlea electrode 105 and driver circuit 101 with casing. The cochlea electrode 105 is installed within the cochlea 122 of a user. The driver circuit 101 is disposed at eardrum 121 of the user with the help of the casing. More particularly, the driver circuit 101 is installed at a through hole on an eardrum 121 of the user. The driver circuit 101 is electrically connected to the cochlea electrode 105 in order to signal process a voice data and provide a corresponding driving signal. Thus, the driving signal will drive the cochlea electrode 105, and then the cochlea electrode 105 will stimulate the auditory nerve cells by electrical stimulation. With the above arrangement, the user could hear the corresponding voice.

The cochlea electrode 105 could be made of different electrode metal wire, for the contacting part that touches cochlea could be made of a relative steady material such as silicone. The cochlea electrode 105 could provide suitable electrical stimulation for stimulates the auditory nerve cells.

The casing of the driver circuit 101 is disposed at a through hole of the eardrum 121, in order to avoid the driver circuit 101 and the cochlea electrode 105 move or slid while use. For instance, a contacting portion of the casing is attached to the through hole on the eardrum 121 in order to locate the driver circuit 101 at an appropriate position. The above said driver circuit 101 could have different designs, such as driver circuit 101 could be made of a verity of digital signal processing circuits, or only include simple current/voltage signal processing units, such as Digital-to-Analog Converter (DAC).

Besides the driver circuit 101 and the cochlea electrode 105, the cochlea hearing aid device further comprises a digital processing circuit for adjusting the voice data. For instance, the digital processing circuit could process a noise reduction, waveform adjustment, or echo cancellation etc. Furthermore, the digital processing circuit could integrated into a corresponding integrated circuit chip.

Figure 2:
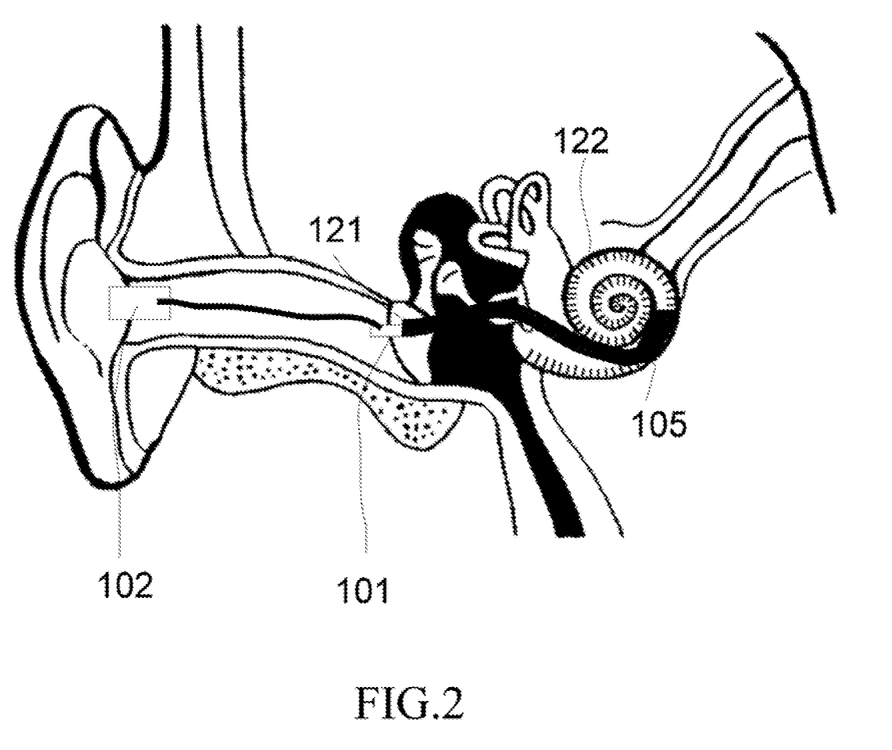
FIG. 2 is a perspective view of the cochlea hearing aid device in accordance with a second embodiment.

Referring to FIG. 2, FIG. 2 is a perspective view of the cochlea hearing aid device in accordance with a second embodiment. The cochlea hearing aid device also comprises a voice amplifier and a voice collector 102. The voice collector 102 might be a microphone for collecting the external sound. The external sound is amplified by the voice amplifier then provides the voice data.

For the second embodiment of the cochlea hearing aid device in FIG. 2, in order to collect a relative clear external sound, the voice collector 102 (such as microphone) could be mounted at external of the ear. For instance, the microphone could mount at external ear and transfer corresponding information via wire or wireless manner to the cochlea electrode.

As the electronic minimizes, these circuit could be made into bar-shaped in order to be placed inside the ear canal making them almost unnoticeable and reduce the psychological reactance of the user. Furthermore, the compact appearance could also increase the mobility.

Figure 3:
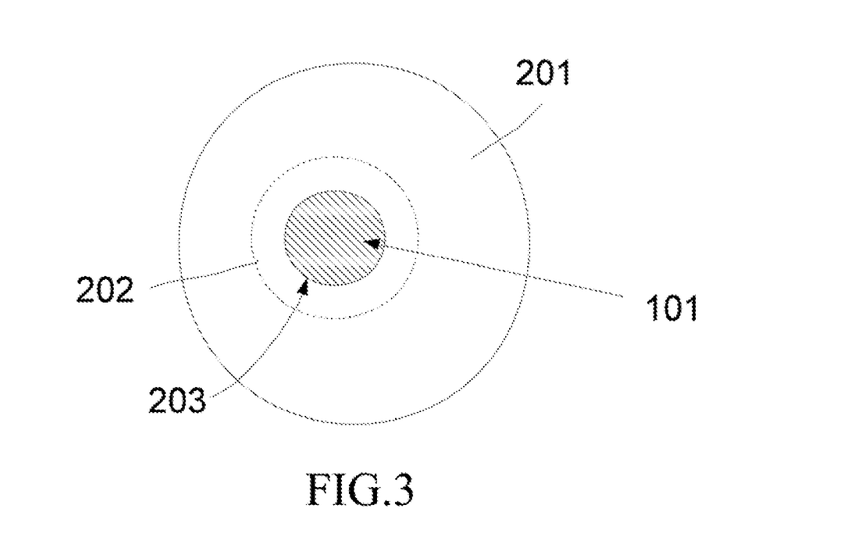
FIG. 3 is perspective view of the cutting wound on the eardrum during the surgery and the healed wound.

Please refer to FIG. 3. FIG. 3 is perspective view of the cutting wound on the eardrum during the surgery and the healed wound. The cochlea hearing aid device should be installed by the assistance of a physician. First, the physician will drill a through hole 202 on the eardrum 201, and above mentioned casing of the driver circuit 101 is mounted on the through hole 202. While the through hole 202 heal to a through hole 203 (healed wound), the driver circuit 101 will be supported and located at an appropriate position.

Figure 4:
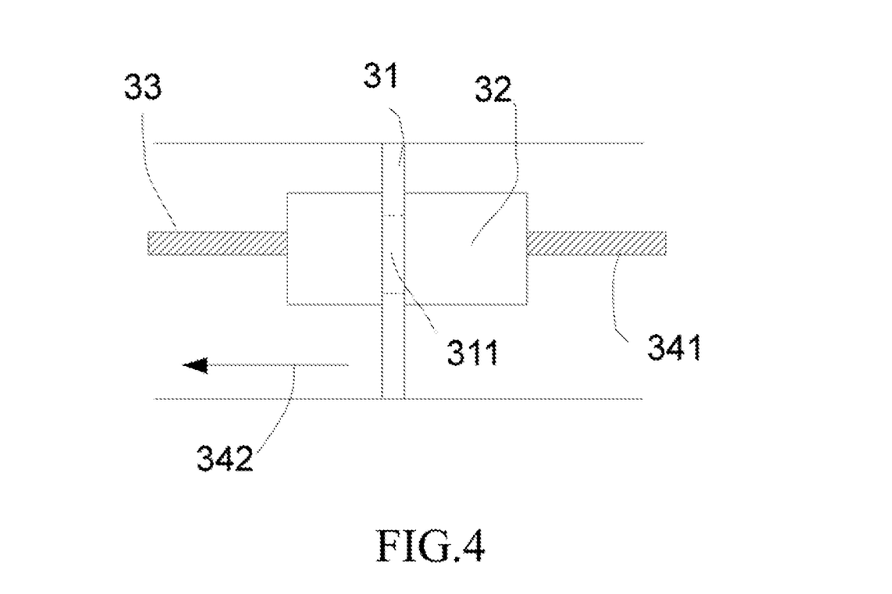
FIG. 4 is a perspective structure of the cochlea hearing aid device of the present invention.

Please refer to FIG. 4, which shows the relationship between the casing 32 of the driver circuit and the eardrum 31. As shown in FIG. 4, at the eardrum 31, a through hole 311 drilled by the physician for hanging and connecting the driver circuit of the cochlea hearing aid device is shown. The casing of the driver circuit extends outward along the cochlea to the cochlea electrode 341 for providing necessary hearing information for user. On the other aspect, in order to lighten the weight of the cochlea hearing aid device that works on the eardrum 31, some element could be mounted at the extending outer casing and connect via signal wires 33. Furthermore, facing outside the ear could also help to collect external voice that needed.

Figure 5:
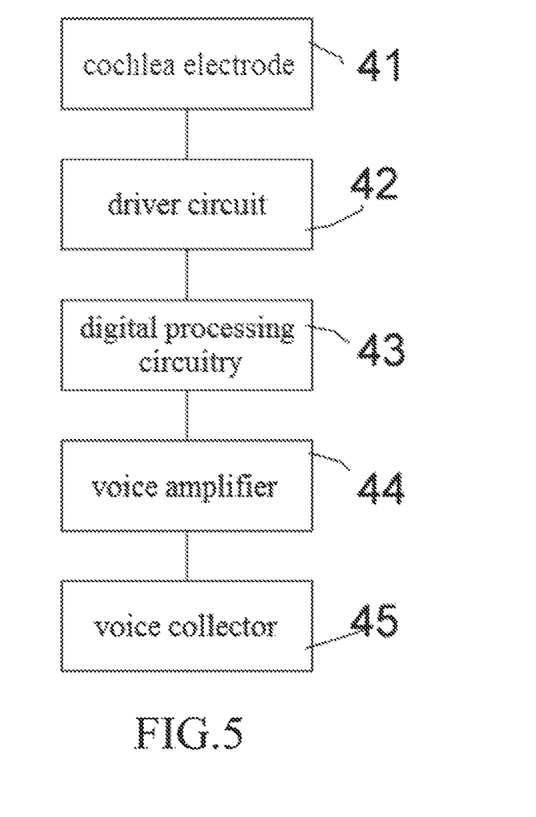
FIG. 5 is an architecture chart of the cochlea hearing aid device of the present invention.

Please refer to FIG. 5. In this embodiment the cochlea hearing aid device includes cochlea electrode 41, driver circuit 42, digital processing circuit 43, voice amplifier 44 and voice collector 45. These circuit and device could be disposed within the same casing or at multiple casings and transmit signal via wireless or wire manner. In the embodiment shown in FIG. 5 the connection between voice amplifier 44 and driver circuit are not limit to wire manner, but also could be connected through a wireless protocol.

Figure 6:
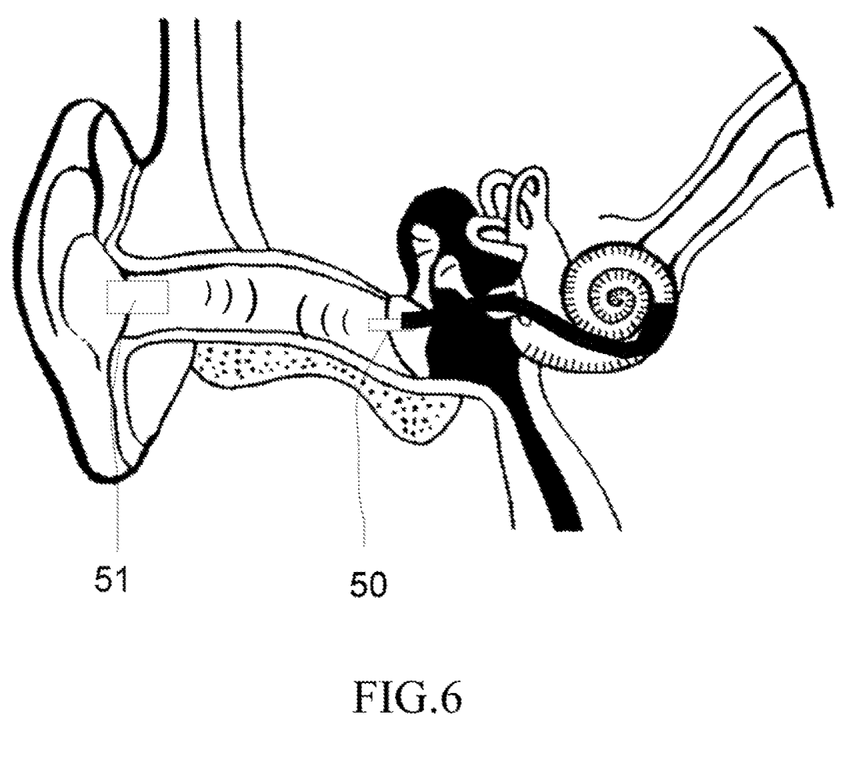
FIG. 6 is a perspective view of another arrangement of the cochlea hearing aid device of the present invention.

Then, please refer to FIG. 6. In FIG. 6, the cochlea hearing aid is made of an inner ear portion 50 and an external ear portion 51. The inner ear portion 50 includes a eardrum housing and a driver circuit, which hanging and connecting to the through hole of the eardrum. The signal transmission between the inner ear portion 50 and the external ear portion 51 is transmitted via a wireless manner. For instance, the voice amplifier that disposed at external ear portion 51 is wireless connected with the driver circuit disposed at inner ear portion 50. In other embodiment, the inner ear portion 50 could be charged by the external ear portion 51. For another possible embodiment, the external ear portion 51 could produce a suitable electromagnetic signal, which could be transmit to corresponding inductor (such as coil) at inner ear portion 50. The electromagnetic signal will vibrates and generates corresponding sound waves.

Figure 7:
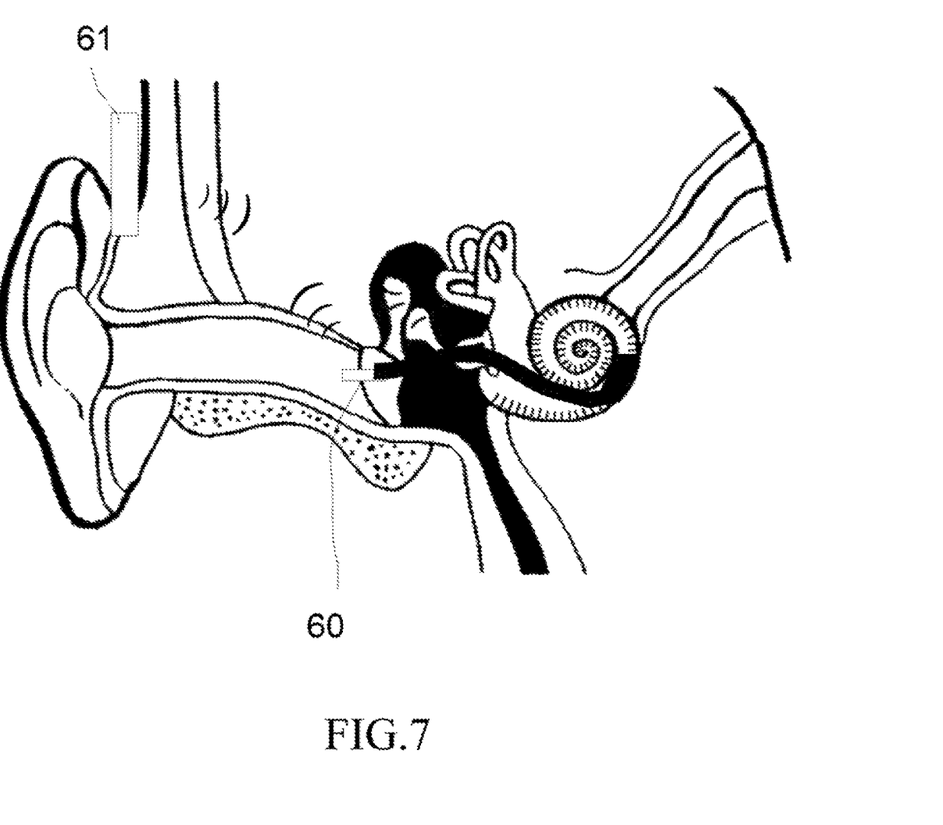
FIG. 7 is a perspective view of other arrangement of the cochlea hearing aid device of the present invention.

Please refer to FIG. 7. Except plugging the external ear portion 61 in the ear of canal via earplug manner, the external ear portion 61 could also hang at the upper ear. Similarly, the external ear portion 61 transfers the collected information via wire or wireless manner to inner ear portion 50.

Figure 8:
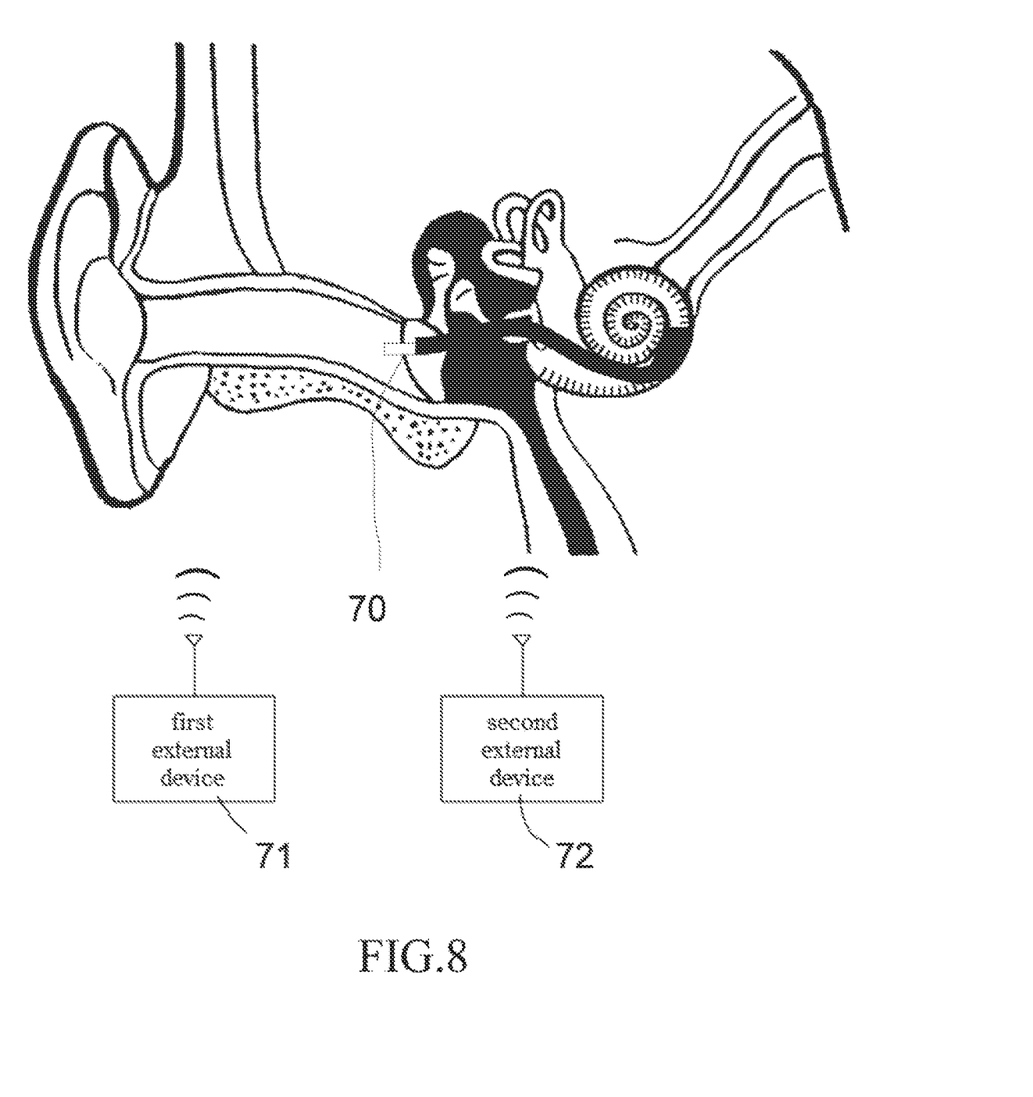
FIG. 8 is drawing for showing how the cochlea hearing aid device interacts with external devices.

Referring to FIG. 8, FIG. 8 shows another possible design that includes at least one or more than one external device. For instance, the cochlea hearing aid includes a first external device 71 and a second external device 72, for directly transmitting signal with the inner ear portion 70 or even for charging the inner ear portion 70. The first external devices 71 could be directly provided by the hearing aid vendor, and the second external devices 72 could be user's own device, such as mobile phone, television or such signal source. The inner ear portion 70 could couple at least one signal source and synthetic voice signal, or could adjust the weight between different voice sources to meet user's need.

Figure 9:
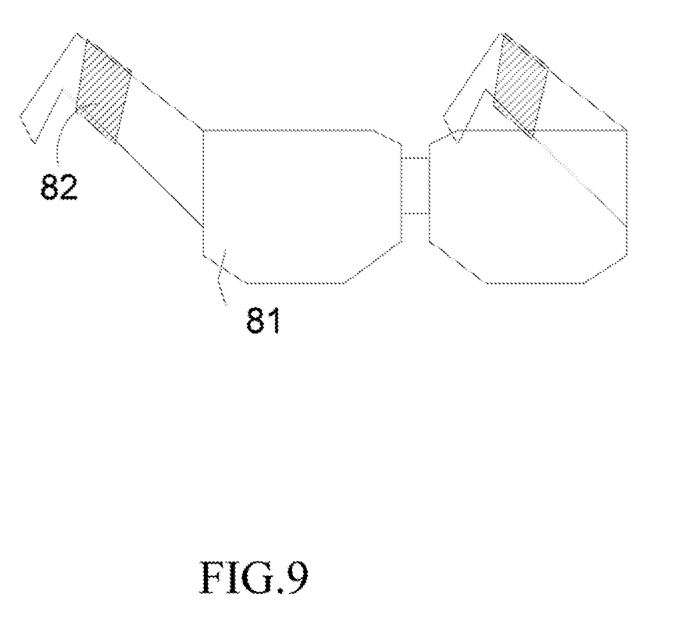
FIG. 9 is perspective view of showing some of the elements of the cochlea hearing aid device mounting on a pair of glass or a pair of smart glass.

As shown in the f FIG. 9, the external ear 82 is mounting on a pair of glass or a pair of smart glass for user to wear. Other variations should be enclosed within the protecting scope of the present invention.

If the information is transmitted via wireless manner, the wireless manner could be any well-known communication protocol, such as blue tooth, wireless USB, ZigBee, Wi-Fi, or any special designed or personal communication protocol.

Other possible solution of the present invention is to include a wireless circuit for eardrum in cochlea hearing aid device. The wireless circuit receives a wireless signal and converts the wireless signal to the voice data. Wherein, the wireless signal is provided by mobile phone or other hand-held electronic apparatus.

Or the cochlea hearing aid device could include a processing circuit that disposed on a pair of glass or a pair of smart glass. The processing circuit could provide the voice data to the driver circuit.

Cochlea electrode could operate in different working modes, wherein different working mode could design different parameters and different working algorithm for voice processing. For instance, while the cochlea electrode connects to an external device such as mobile phone, some of the computing progress could be outsourced to mobile phone. In order to save power, the cochlea electrode that corresponding to the inner ear portion only need to provide basic function like voice output. Further, the voice data could also process difficult data processing via an external hand-held electronic apparatus to meet the requirement of different design of the hearing aids.

The wireless signal further comprises a controlling signal for adjusting the output parameter of the cochlea electrode. For instance, the cochlea hearing aid devices at different ears could be adjusted to provide corresponding output parameter to avoid the uncomfortable feeling cause by hearing difference in each ear.

The cochlea hearing aid device further include a power circuit for eardrum that provides the power to the cochlea electrode and the driver circuit via wire or wireless manner. As the technique of the wireless charging improved, many wireless charging methods can apply with the cochlea hearing aid device and provide a more life convenient hearing aid.

For those with normal hearing, acoustic perception includes direction and distance. In order to imitate normal acoustic perception, voice processing of the cochlea hearing aid device further includes a voice signals with a direction perception. For example, in one of the embodiments, multiple microphones could be placed in different positions for collecting external sound. Since placing in different positions, there are transmitting shifts among the collected sounds. When user use a pair of cochlea hearing aid device, the cochlea hearing aid device could adjust each of the corresponding parameter of the cochlea electrode (respect to different ears). Through the adjustment, voice signals with different direction perceptions could be provide to each eardrum for hearing. Therefore, one could percept the direction and distance of the object that provides sounds in order to response or act. The object that provides sounds could be vehicles or stepping sounds.

Furthermore, one's acoustic perception could also affect one's balance control. For a more comfortable cochlea hearing aid device wearing experience, the cochlea hearing aid device could provide different parameters and adjustment according to different ears. These parameter adjustments might need to adjust according to different scenarios and a might need a relative longer adjusting period. The corresponding configuration could be saved at a mobile phone or hand-held electronic apparatus. User could set several scenario parameters and adjust different output parameters for different ears according to need. For example, watching television, attending class, during conversation, self-talking while learning language could be set as different scenarios. With the above means, user could simply select between the scenarios for the corresponding parameter to output suitable voice output. An auto select could be applied through the help of information like GPS, Wi-Fi signal and time.

In addition, the voice signals are processed signals, therefore the voice signals do not have to be exactly like the origin voice signal from the outside. In other way of speaking, the voice data could go through a translating process in order to translate the origin voice signal from the outside to a corresponding a voice signal with a replaced content. For example, the translating process could be a foreign language translating process, and translates the received foreign language to an understandable language for user. The translating process could be a dialect translating process for translating an unfamiliar dialect language to a familiar dialect language or official language for user.

For example, the voice data could extract portion of the origin voice signal from the outside and repeatedly play. Or in other example, the voice data will extract at least one keyword from the origin voice signal from the outside, and at least one keyword is accentuated and played. The original voice signal is analyze and keywords are extracted, and only keywords are outputted. For those elders that suffer from cognitive impairment, repeating keywords from the origin voice signal several times could help them to pick up the message inside the voice signal more easily. Others, the voice signal could be recorded, selected and replayed by the user. The origin voice signal from the outside could be sounds directly provided by the object or could be sounds generates by the electric device such as alarm sound. Other than that, the voice signal could be the result of language translating process, a result of dialect translating process, a result of accentuated process or a result of speed adjusted process.

For instance, some elders can only speak and understand dialects, but their grandchildren could only speak official language. In this case, the translating process could be set to a mode that could translate the dialect to the official language (i.e., a dialect translating process). Further, with the aid of recording and replaying, the communication between the elder and the youth will be improved and provide positive effect on the quality of life.

The present invention is described as above with the foregoing preferred embodiments, but the embodiments are not intended to limit the present invention. Any person skilled in the art can make some variations and modifications without departing from the spirit and scope of the present invention. Therefore, the patent protection scope of the present invention should be subject to that defined by the claims appended to the specification.

What is claimed is:

1. A cochlea hearing aid device for helping user to hear, comprising:
    a cochlea electrode, disposed at the cochlea of a user;
    a driver circuit, comprising a casing that is configured to be installed at a through hole on the eardrum of the user, and the driver circuit being electrically connected to cochlea electrode, wherein the driver circuit signal processes a voice data in order to provide a corresponding driving signal for driving the cochlea electrode; and
    a plurality of hand-held electronic apparatuses transmitting different wireless signals to the driver circuit respectively, and the driver circuit synthesizing received wireless signals, wherein at least one of hand-held electronic apparatuses stores a plurality of scenario parameters, and transmits a controlling signal to the driver circuit based on a selected scenario parameter, wherein the driver circuit adjusts an output parameter of the cochlea electrode according to the controlling signal transmitted by the hand-held electronic apparatus.

2. The cochlea hearing aid device of claim 1, wherein a contacting portion of the casing is attached to the through hole on the eardrum in order to locate the driver circuit at an appropriate position.

3. The cochlea hearing aid device of claim 1, further comprising a digital processing circuit for generating and adjusting the voice data.

4. The cochlea hearing aid device of claim 1, further comprising a voice amplifier and a voice collector, wherein the voice collector collects an external sound and the external sound is amplified by the voice amplifier then provides the voice data.

5. The cochlea hearing aid device of claim 4, wherein the voice amplifier and the driver circuit are connected via a signal wire.

6. The cochlea hearing aid device of claim 4, wherein the voice amplifier and the driver circuit are configured to communicate via wireless protocol.

7. The cochlea hearing aid device of claim 1, further comprising a wireless circuit disposed within the driver circuit for receiving the wireless signal and converting the wireless signal to the voice data.

8. The cochlea hearing aid device of claim 7, further comprising a processing circuit being disposed on a pair smart glass, the processing circuit providing the voice data to the driver circuit.

9. The cochlea hearing aid device of claim 1, wherein at least one of the hand-held electronic apparatuses is a mobile phone.

10. The cochlea hearing aid device of claim 1, further comprising a power circuit disposed within the driver circuit that provides the power to the cochlea electrode and the driver circuit.

11. The cochlea hearing aid device of claim 10, wherein the power is transmitted from the power circuit for eardrum to driver circuit via wireless manner.

12. The cochlea hearing aid device of claim 10, wherein the user uses a pair of the cochlea hearing aid devices, and the output parameter of the cochlea electrodes of each cochlea hearing aid device is adjustable respectively.

13. The cochlea hearing aid device of claim 12, wherein the cochlea electrodes provide different corresponding voice signals with a direction perception to the eardrum for helping the user to hear.

14. The cochlea hearing aid device of claim 1, wherein through a translating process the origin voice signal from the outside is translated to a corresponding voice signal with a replaced content.

15. The cochlea hearing aid device of claim 14, wherein the voice data extracts portion of the origin voice signal from the outside and repeatedly plays.

16. The cochlea hearing aid device of claim 14, wherein the translating process is a foreign language translating process.

17. The cochlea hearing aid device of claim 14, wherein the translating process is a dialect translating process.

18. The cochlea hearing aid device of claim 1, wherein the voice data extracts at least one keyword form the origin voice signal from the outside, and at least one keyword is accentuated.

19. The cochlea hearing aid device of claim 1, wherein the driver circuit adjusts weight of different wireless signals according to the controlling signal.

* * * * *